United States Patent
Kretschmer et al.

(10) Patent No.: US 6,352,556 B1
(45) Date of Patent: Mar. 5, 2002

(54) VERTEBRAL COLUMN REPLACEMENT BODY

(75) Inventors: Peter Kretschmer, Bruchköbel; Uwe Siedler, Alzenau, both of (DE)

(73) Assignee: Signus Medizintechnik GmbH, Alzenau (DE)

( * ) Notice: Subject to any disclaimer, the term of this patent is extended or adjusted under 35 U.S.C. 154(b) by 0 days.

(21) Appl. No.: 09/489,816

(22) Filed: Jan. 24, 2000

(30) Foreign Application Priority Data

Jan. 22, 1999 (DE) .......................................... 199 02 481

(51) Int. Cl.$^7$ .................................................. A61F 2/44
(52) U.S. Cl. .................................. 623/17.11; 623/17.15
(58) Field of Search .......................... 623/17.11, 17.15, 623/17.16, 17.13

(56) References Cited

U.S. PATENT DOCUMENTS

| | | | |
|---|---|---|---|
| 5,290,312 A | * | 3/1994 | Kojimoto et al. ......... 623/17.11 |
| 5,723,013 A | * | 3/1998 | Jeanson et al. .......... 623/17.11 |
| 5,800,547 A | * | 9/1998 | Schafer et al. ........... 623/17.11 |
| 6,015,436 A | * | 1/2000 | Schonhoffer ............. 623/17.11 |
| 6,176,881 B1 | * | 1/2001 | Schar et al. ............. 623/17.11 |
| 6,193,756 B1 | * | 2/2001 | Studer et al. ............ 623/17.15 |

FOREIGN PATENT DOCUMENTS

DE 297 03 043 2/1997

* cited by examiner

*Primary Examiner*—Corrine McDermott
*Assistant Examiner*—Suzette Jackson
(74) *Attorney, Agent, or Firm*—Friedrich Kueffner

(57) ABSTRACT

A vertebral column replacement body or spacer has first and second anchoring sides each facing in the mounted or implanted state of the body an adjacent vertebra, wherein each anchoring side has a tooting for ensuring that displacement in the ventral or dorsal directions is safely prevented. The vertebral column replacement body has two body elements which are slidingly guided relative to each other and transversely of the anchoring sides, wherein, after a desired relative position has been reached, a first body element can be braced against the second body element by radially widening the first body element.

5 Claims, 1 Drawing Sheet

VERTEBRAL COLUMN REPLACEMENT BODY

BACKGROUND OF THE INVENTION

1. Field of the Invention

The present invention relates to a vertebral column replacement body or spacer with first and second anchoring sides each facing in the mounted or implanted state of the body an adjacent vertebra, wherein each anchoring side has a tooting for ensuring that displacement in the ventral or dorsal directions is safely prevented.

2. Description of the Related Art

In conventional vertebral column replacement bodies of this type, as disclosed, for example, in DE GM 297 03 043, the two anchoring sides of the approximately parallelepiped-shaped body have a fixed predetermined distance between each other. Consequently, the possibilities for using this replacement body or spacer are limited.

SUMMARY OF THE INVENTION

Therefore, it is the primary object of the present invention to further develop the conventional vertebral column replacement body in such a way that it can be adjusted to the existing conditions of use.

In accordance with the present invention, the vertebral column replacement body has two body elements which are slidingly guided relative to each other and transversely of the anchoring sides, wherein, after a desired relative position has been reached, a first body element can be braced against the second body element by radially widening the first body element.

Because of the infinitely variable length adjustment capability of this vertebral column replacement body or spacer, the replacement body or spacer can be adapted in an optimum manner to the locally existing conditions of a patient.

It has been found to be very useful for this purpose if the first body element has two, or preferably several, segments extending approximately parallel to the axis away from the first anchoring side, wherein the segments are bendable relative to each other in the radial direction by means of a tightening screw which acts transversely of its direction of extension.

In a preferred embodiment of this vertebral column replacement body, the second body element has a wall extending away from the second anchoring side, wherein the segments of the first body element can be placed in tight contact with the wall by means of the tightening screw.

In accordance with a particularly advantageous feature, the single tightening screw extends radially through a threaded bore of a segment of the first body element and the tightening screw acts with its front end on the other segments of the first body element.

In accordance with another advantageous further development of the vertebral column replacement body according to the present invention, a particularly uniform force application and, thus, bracing of the two body elements, is achieved by providing three segments in the first body element and by having the tightening screw extending through one segment protrude with its front end into the area between the two other segments in order to simultaneously apply a radial force.

In accordance with a useful feature, the first body element is constructed in the form of a cylindrical cup which is divided into three segments of equal size by providing slots extending parallel to the axis and with the same angular spacing up to below the edge forming the first anchoring side, wherein the first segment has the threaded bore which is directed towards the slot between the two other segments. The bottom of the cup advantageously has a thickness which is greater than the diameter of the threaded bore for receiving the tightening screw and, thus, is significantly greater than the wall thickness of the cup.

A particularly elegant embodiment of the vertebral column replacement body is obtained if the tightening screw is formed by a headless screw which does not protrude above the threaded bore with its end provided for the slot for applying a screwdriver.

As mentioned above, the length of the range within which an infinitely variable adjustability of the spacing between the anchoring sides of the two body elements exists can be freely selected. For this purpose, the second cylindrically constructed body element has an oblong hole extending along its circumferential line, wherein a screwdriver can be placed through the oblong hole for acting on the tightening screw, and wherein the length of the oblong hole determines the extent of the possible height adjustment.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
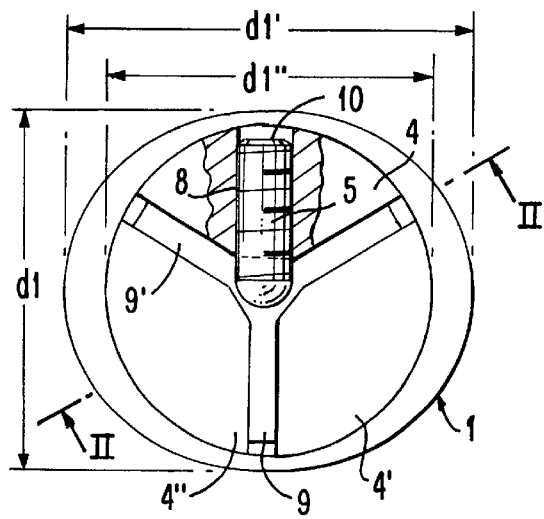
FIG. 1 is a front view of an end of the first body element of the vertebral column replacement body according to the present invention.
Figure 2:
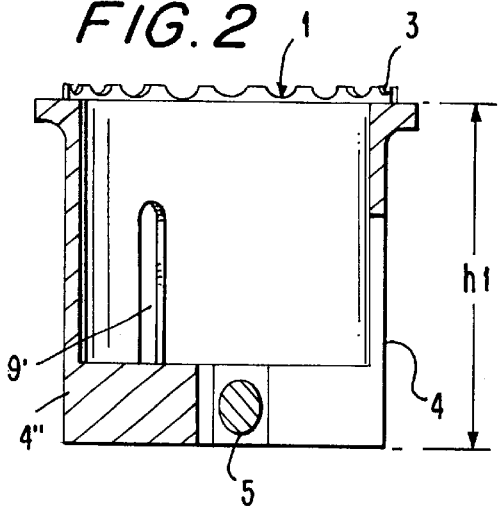
FIG. 2 is a sectional view of the first body element taken along sectional line II—II of FIG. 1.
Figure 3:
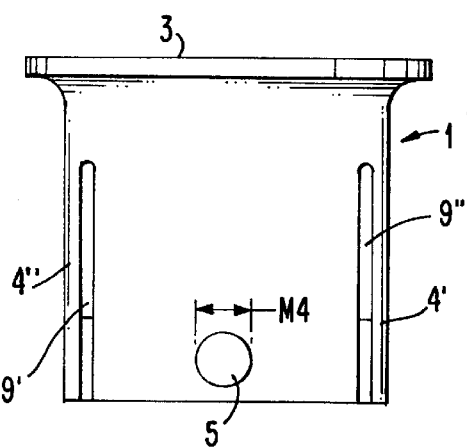
FIG. 3 is a side view of the body element of FIG. 1.
Figure 4:
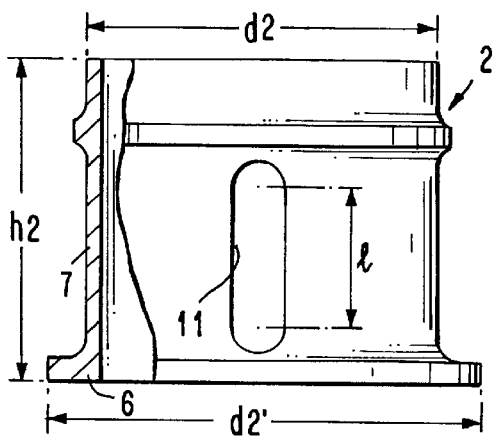
FIG. 4 is a side view, partially in section, of the second body element which together with the first body element forms the vertebral column replacement body.
Figure 5:
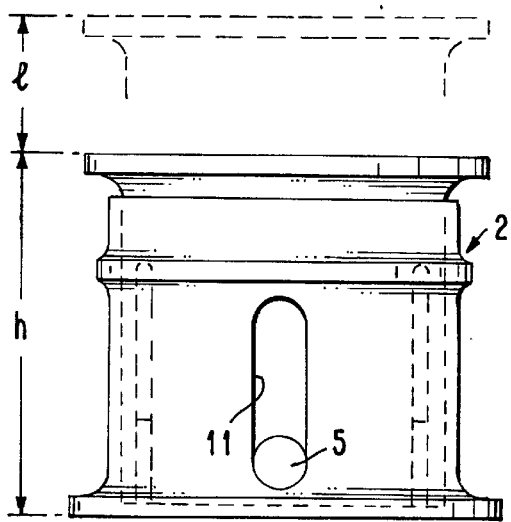
FIG. 5 is a side view of the second body element of FIG. 4 with a schematically illustrated first body element inserted into the second body element.

As is apparent from the drawing, the vertebral column replacement body according to the present invention is formed by two body elements which are slidable relative to each other. The body elements are a first body element 1 which is shown in FIGS. 1 through 3, and a second body element 2 which is illustrated in FIGS. 4 and 5. The first body element 1 has a plurality of segments 4, 4', 4" which extend approximately parallel to the axis of the replacement body and away from the first anchoring side 3 of the replacement body. The segments can be bent relative to each other in the radial direction by means of a tightening screw 5 which acts transversely of the direction of extension thereof. As seen in FIG. 2, a tooting for preventing displacement in the ventral or dorsal directions is provided on an anchoring side 3 of the first body element 1. All other anchoring sides of the vertebral column replacement body are also provided with this toothing.

The second body element 2 has a wall 7 which extends away from the second anchoring side 6, wherein the segments 4, 4', 4" of the first body element 1 can be placed in tight contact with the wall 7 by applying a force with the tightening screw. In this manner, after the desired relative position between the two body elements has been reached, the body elements 1, 2 which are slidably guided relative to each other transversely of the anchoring sides 3 and 6, can be braced relative to each other by radial expansion.

As is apparent from the drawing, only a single tightening screw 5 is sufficient which radially extends through a threaded bore 8 of one of the segments 4 of the first body element 1 in order to act with its front end on the two other segments 4' and 4", and thereby to produce the radial expansion of the first body element 1, so that the first body element 1 is placed in tight contact with the inner side of the wall 7 of the second body element 2 and a relative displacement is prevented.

For preventing a displacement of the vertebral column replacement body in the plane of the anchoring sides, i.e., in the ventral and dorsal directions, the anchoring sides are provided with a tooting which is known in the art and is not illustrated in detail. This tooting may be provided directly on the anchoring sides 3, 6 or on an outer closing surface element which can be placed on the anchoring sides 3, 6 and can be tightly connected thereto.

The drawing further shows that the first body element 1 is constructed in the form of a cylindrical cup which is divided into three segments 4, 4', 4" of equal size by slots 9, 9', 9" which extend parallel to the axis of the replacement body up to underneath the edge forming the first anchoring side 3 and are arranged at equal angular spacings of 120°. The first segment 4 has the threaded bore 8. As can be seen in FIG. 1, the threaded bore 8 is directed towards the slot 9 between the two other segments 4', 4". As illustrated, the bottom of the cup of the first body element 1 has a thickness which is greater than the diameter of the threaded bore for receiving the tightening screw, wherein, in the illustrated embodiment, the tightening screw has a M4 thread and, thus, is substantially greater than the wall thickness of the cup.

As particularly shown in FIG. 1, the tightening screw is a headless screw which in the mounted state does not protrude above the threaded bore 8 with its head which is provided with the slot 10 for applying a screwdriver.

As shown in FIGS. 4 and 5, the second cylindrically constructed body element 2 has an oblong hole 11 which extends on its circumference in the axial direction, wherein a screwdriver can be placed through the oblong hole for acting on the tightening screw 5, and wherein the length l of the oblong hole determines the extent of the possible vertical adjustment.

In a practical embodiment, the length l is 10 mm. The height h1 of the first body element 1 is about 25 mm, the diameter d1 of the oval edge forming the surface of the anchoring side 3 is about 26 mm, the largest diameter d1' is about 30 mm and the inner diameter d1" of the anchoring side 3 is about 24 mm.

The height h2 of the second cylindrically constructed body element 2 is about 23 mm and the diameter d2 is about 26 mm. The maximum diameter d2' is about 32 mm.

The invention is not limited by the embodiments described above which are presented as examples only but can be modified in various ways within the scope of protection defined by the appended patent claims.

We claim:

1. A vertebral column replacement body comprising first and second anchoring sides each adapted to face in a mounted state of the vertebral column replacement body an adjacent vertebra, wherein each of the anchoring sides comprises a tooting for preventing displacement in the ventral or dorsal directions, further comprising two body elements mounted so as to be slidingly guided relative to each other and transversely of the anchoring sides, wherein, when a desired relative position between the body elements is reached, a first of the body elements is configured to be braced against a second of the body elements by radially widening the first body element, wherein the first body element comprises a plurality of segments extending approximately parallel to an axis of the vertebral column replacement body and away from the first anchoring side, further comprising a tightening screw extending radially through a threaded bore of one of the segments of the first body element and acting transversely of a direction of extension thereof for bending the segments relative to each other in a radial direction against a wall of the second body element extending away from the second anchoring side, wherein the tightening screw is configured to place the segments of the first body element in tight contact with the wall, wherein the first body element has a first segment, a second segment and a third segment, and wherein the tightening screw extends through the first segment and the front end of the tightening screw protrudes into an area between the second and third segments for simultaneously radially acting on the segments.

2. The vertebral column replacement body according to claim 1, wherein the first body element is comprised of a cylindrical cup, wherein the first, second and third segments are formed by three slots of the cup extending parallel to the axis up to underneath an edge forming the first anchoring side, wherein the slots are arranged at equal angle distances such that the segments are of equal size, wherein the first segment has the threaded bore and the threaded bore is aligned with a slot between the second and third segments.

3. The vertebral column replacement body according to claim 2, wherein the cup has a bottom wall with a thickness which is greater than a diameter of the threaded bore for receiving the tightening screw and significantly greater than a side wall thickness of the cup.

4. The vertebral replacement body according to claim 1, wherein the tightening screw is a headless screw having an end with a slot adapted for receiving a screw driver, wherein the end of the screw does not protrude beyond the threaded bore.

5. The vertebral replacement body according to claim 4, wherein the second body element is cylindrically shaped and has an oblong hole extending along a circumferential line thereof, wherein the oblong hole is configured to receive a screw driver for acting on the tightening screw, and wherein a length of the oblong hole determines an extent of an adjustment in the axial direction.

\* \* \* \* \*